(12) United States Patent
Bosco

(10) Patent No.: US 7,172,564 B2
(45) Date of Patent: Feb. 6, 2007

(54) AUTOMATIC DEVICE FOR OPTIMIZED MUSCULAR STIMULATION

(75) Inventor: Carmelo Bosco, Rome (IT)

(73) Assignees: Olga Tsarpela, Rome (IT), part interest; Alessandro Bosco, Rome (IT), part interest; Carla Marta Stefania Bosco, Jyvaskyla (FI), part interest; Manuela Anna Maria Bosco, Jyvaskyla (FI), part interest ( * ) Notice: Subject to any disclaimer, the term of this patent is extended or adjusted under 35 U.S.C. 154(b) by 538 days.

(21) Appl. No.: 10/182,675

(22) PCT Filed: Jan. 16, 2001

(86) PCT No.: PCT/IT01/00020

§ 371 (c)(1),
(2), (4) Date: Nov. 13, 2002

(87) PCT Pub. No.: WO01/56650

PCT Pub. Date: Aug. 9, 2001

(65) Prior Publication Data

US 2003/0135140 A1    Jul. 17, 2003

(30) Foreign Application Priority Data

Jan. 31, 2000    (EP) .................................. 00830072

(51) Int. Cl.
*A61H 1/00*    (2006.01)

(52) U.S. Cl. ........................................................ 601/46

(58) Field of Classification Search ................ 600/546, 600/552, 554; 607/48–50; 601/15, 23, 30, 601/31, 34, 35, 46, 48, 53, 67, 69, 70, 71, 601/78, 79, 84, 89, 90, 93, 97, 98, 101
See application file for complete search history.

(56) References Cited

U.S. PATENT DOCUMENTS

| 4,838,272 | A |   | 6/1989 | Lieber |
| 5,012,820 | A | * | 5/1991 | Meyer ........................ 600/554 |
| 5,507,788 | A |   | 4/1996 | Lieber |
| 5,702,429 | A |   | 12/1997 | King |
| 5,722,420 | A |   | 3/1998 | Lee |
| 6,010,468 | A |   | 1/2000 | Grove et al. |

FOREIGN PATENT DOCUMENTS

| EP | 0 811 364 A2 | 12/1997 |
| GB | 535937 | 4/1941 |

* cited by examiner

*Primary Examiner*—Quang D. Thanh
(74) *Attorney, Agent, or Firm*—Young & Thompson

(57) ABSTRACT

An automatic device for optimized muscular stimulations, includes a central electronic unit connected to a memory unit, to muscular electrical activity detectors, and to muscular stimulation elements. The central unit determines within a range included between a lower limit frequency and an upper limit frequency, an optimum frequency of the periodical contractions in correspondence of which the sum of the amplitude of the signals provided by the detectors from the corresponding muscles of the user as a response to the stimulation is the maximum one. The central unit sets the muscular stimulation elements to produce periodical contractions of the muscle to be stimulated at the determined optimum frequency.

21 Claims, 2 Drawing Sheets

AUTOMATIC DEVICE FOR OPTIMIZED MUSCULAR STIMULATION

BACKGROUND OF THE INVENTION

The present invention relates to an automatic device for optimized mechanical muscular stimulation and/or stressing.

More specifically, the invention concerns a device of the above kind, the stimulation of which, preferably mechanically produced, provides constant frequency periodic contractions of a muscle of a user, providing the preliminary detection of the frequencies of the periodic contractions corresponding to the best electromyographycal response for the muscle to be stimulated, and a following stimulation of the same muscle at the optimum frequency sensed, the device being highly reliable and efficient.

DESCRIPTION OF THE RELATED ART

It is known that when a muscle is stimulated by application of mechanical vibrations, it contracts in a reflex way very similarly to what happens when the muscle is operated by voluntary contractions, e.g. during the execution of physical works.

Particularly, varying the frequency of the mechanical vibrations, it is possible to make selectively working fast or slow muscular fibers.

Recently, many mechanical devices for the muscular stimulation have been developed, such as a board, for the leg muscles, or a vibrator, for the arm muscles.

Said devices are useful for training of agonistic level athletes, since they allow to obtain the same results of the standard physical exercises within the gymnasium in a shorter time, to obtain a good muscular tone by few application minutes at home, and for physical therapy uses aimed to the maintenance of the muscular tone or to the functional recover of the muscles, for example during or after immobilization periods due to fractures or surgical intervention.

However, present mechanical muscular stimulation devices have some drawbacks.

Main drawback is represented by the fact that the mechanical vibration frequency, that can be manually set, is not optimized either for the specific fibers of a determined muscle of the specific user and for the whole body.

In fact, specific fibers of any muscle of any single user has a response to the micro-vibrations variable while varying the frequency of the applied vibration. Particularly, it can be individuated a frequency range, which can be defined "activity range", within which specific fibers of the particular muscle respond to the stimulations and, within said range, it can be determined an optimum mechanical frequency in correspondence of which said response is the maximum one. In case the set frequency is different with respect to the optimum one, the work of the interested muscle is not efficient for its toning up and, in case frequency set is not included within the activity range, muscular work is completely null. In some cases, the wrong set of the vibration frequency could even produce harmful results.

Similar drawbacks are present in electrical muscle stimulation devices, the frequency of the electrical signal of which, applied to the specific muscle, is not optimized.

In this situation, it is suggested the solution according to the present invention, allowing to solve all the above mentioned drawbacks.

SUMMARY OF THE INVENTION

Therefore, the object of the present invention is that of providing a preferably mechanical device, which is reliable, efficient and simple to be used, for the muscular stimulation, able to determine in an automatic way the optimum periodic stimulated contraction frequency for which the specific fibers of the particular interested muscle have the maximum, not only muscular, but also generally speaking biological, response.

Still an object of the present invention is that of providing such a device for the muscular electro-stimulation, able to automatically determine the optimum frequency of the electronic signal to be applied at the particular interested muscle in such a way to stimulate periodic contractions with an optimum frequency.

It is therefore specific object of the present invention an automatic device for optimized muscular stimulation, the stimulation providing periodic contractions with constant frequency of one or more muscles of a user, the device comprising a central electronic unit, connected to a memory unit, to one or more muscular electrical activity detectors, each one applied on a corresponding muscle of the user to be subjected to stimulation, and to muscular stimulation means actuated by the central unit, the central unit managing and controlling the automatic device, processing the data coming from the detectors in such a way to determine, within a range included between a lower limit frequency and an upper limit frequency, an optimum frequency of the periodic contractions in correspondence of which the average of the amplitude of the signals provided by the detectors from the corresponding muscles of the user as a response to the stimulation is the maximum one, the central unit setting the muscular stimulation means in such a way to produce periodic contractions of the muscle to be stimulated at the determined optimum frequency.

Preferably, according to the invention, the lower limit frequency is 1 Hz and/or the upper limit frequency is 1000 Hz.

Still preferably, according to the invention, muscular stimulation means are mechanical means.

Always according to the invention, the mechanical means can provide a support structure on which a jumpy board is placed, on which the user is placed, comprising a metallic plate at which at least engine is coupled having an eccentric mass, able to produce the vibration of the plate, piloted by an electronic device comprising an inverter connected to a potentiometer adjusting the vibration frequency, the central unit setting said vibration frequency.

Furthermore according to the invention, the mechanical means can provide a support structure on which a tilting board is placed.

Still according to the invention, the muscular stimulation means can be electrical means.

Further, according to the invention, the detector can comprise medical electrodes, amplified in situ, an insulation amplifier and a signal converter providing at the outlet a digital signal read by the central unit.

Always according to the invention, each one of said one or more detectors can comprise medical electrodes, amplified in situ, an insulation amplifier and a signal converter providing at the outlet a digital signal read by the central unit.

Furthermore, according to the invention, the central unit can follow a determination method of the optimum frequency comprising the phases of:

application of said one or more detectors to the corresponding muscles to be stimulated;

repetition for N times, preferably eight times, of a data acquisition phase during which the central unit actuates the stimulation means in such a way to produce periodic contractions of the muscle with a constant frequency for a Δt time, preferably between 5 and 10 seconds, with a progressively growing frequency, from a repetition to the following one and included between the lower limit frequency and the upper limit frequency, processing, for each repetition, the average of the amplitude of signals coming from the detectors and memorizing the same within the memory unit along with the value of the corresponding frequency; and determination of the maximum value of the average of the amplitude of signals detected by said detectors, wherein the central unit determines, between those memorized, the averages at the same frequency having the maximum value, individuating the optimum frequency.

Still according to the invention, consecutive repetition frequencies can have each other a constant difference.

Furthermore, according to the invention, the consecutive repetition frequencies can have a difference variable and increasing as a function of the absolute value of the frequency of the preceding repetition.

Still according to the invention, the central unit can perform a determination method of the optimum frequency, comprising the phases of:

application of said one or more detectors to the corresponding muscles to be stimulated;

iteration for M times, preferably two times, of cycles of a number $N_i$ of repetitions, wherein i is the i-th repetition, of data acquisition phases during which the central unit actuates the stimulation means in such a way to produce periodic contractions of the muscles with a constant frequency for a Δt time, preferably between 5 and 10 seconds, with a progressively growing frequency, from a repetition to the following one and included between the lower limit frequency and the upper limit frequency, frequencies of consecutive repetitions having each other a constant difference $\Delta f_i$, the central unit processing, for each repetition, the average of th amplitude of signals coming from the detectors and memorizing it within the memory unit along with the value of the corresponding frequency, the central unit determining for each iteration i the maximum value of the average of the amplitudes of the signals detected and individuating the corresponding best frequency for each iteration i, following the first one, the range between the first lower frequency and the second upper frequency comprising the best frequency individuated at the preceding iteration, for each iteration i, following the first one, the constant difference Δfi between the consecutive repetition frequencies being lower than the difference $\Delta f_i-1$ of the preceding iteration ($\Delta f_i < \Delta f_{i-1}$); and determination of the optimum frequency at the end of the M-th iteration, wherein the best frequency individuated at the M-th iteration is memorized as the optimum frequency.

Preferably, according to the invention, for the first iteration, the first lower frequency coincides with the lower limit frequency and/or the second upper frequency, with the upper limit frequency.

Still preferably according to the invention, for each iteration i following to the first one, the range between the first lower frequency and the second upper frequency comprises the best frequency individuated at the preceding iteration as intermediate frequency.

Furthermore, according to the invention, the automatic device can also comprise an inlet/outlet interface, preferably comprising a display.

Always according to the invention, the central unit can visualize on the display signals detected by detectors and the value of the optimum frequency individuated.

Still according to the invention, the device can provide, by the interface, the manual setting selection of the periodic contractions of the muscle.

Furthermore, according to the invention, the interface can be provided with reading and writing devices for removable memory.

BRIEF DESCRIPTION OF THE DRAWINGS

The present invention will be now described, for illustrative but not limitative purposes, according to its preferred embodiments, with particular reference to the figures of the enclosed drawings, wherein.

DESCRIPTION OF THE PREFERRED EMBODIMENTS

In the following explicit reference will be made for illustrative but not limitative purposes to an embodiment of the device according to the invention the stimulation means of which are mechanical means. However, it must be noted that other embodiments of the device according to the present invention can provided where the muscular stimulation means are electrical or electromechanical means, always remaining within the scope of the present invention.

Figure 1:
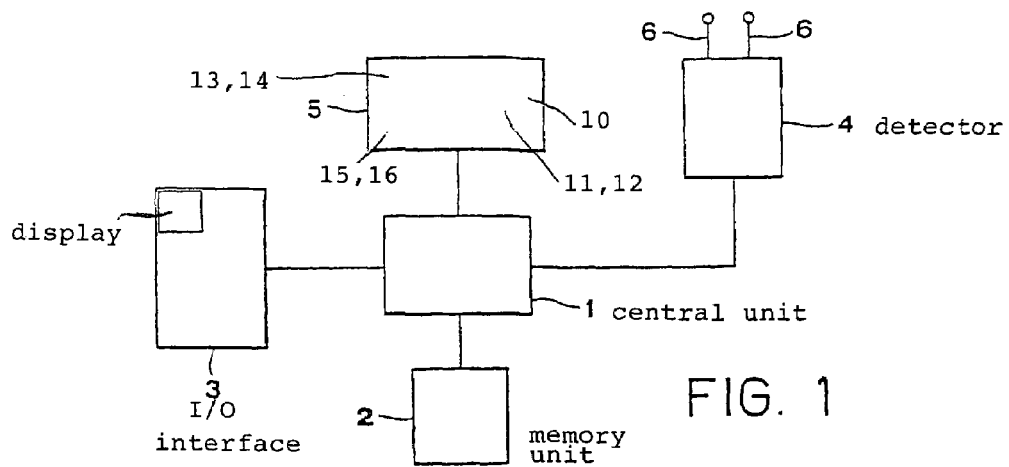
FIG. 1 shows a block diagram of the preferred embodiment of the device according to the invention.

Making reference to FIG. 1, it can be noted that the preferred embodiment of the device according to the invention comprises a central electronic unit 1, connected to a memory unit 2 and to an inlet/outlet interface 3. Central unit 1 is also connected to a detector 4 of muscular electric activity and to mechanical stimulation mechanical means 5.

Detector 4 comprises medical electrodes 6, amplified in situ, an insulation amplifier and a signal converter providing at the outlet a digital signal read by the central unit 1.

Mechanical means 5 provides, in the preferred embodiment, for the stimulation of the leg muscles, a support structure on which a jumpy board 10 is placed, on which the user is placed, comprising a metallic plate 11, resting on rubber shims 12 thereby allowing its vibration. Two engines 13 are coupled with the plate, having eccentric masses 14, able to produce the vibration of the plate, piloted by an electronic device comprising an inverter 15 connected to a potentiometer 16 adjusting the vibration frequency, the central unit setting said vibration frequency. Particularly, central unit 1 sets said vibration frequency. Support structure can provide a rod or handle for the user.

As it known, the vibration mechanical frequency of the mechanical means 5 of the stimulation coincides with the frequency of the periodic contractions of the muscle induced by the stimulation.

Central unit 1 manages and controls all the components of the automatic device, processing data coming from detector 4 in such a way to determine within said range included between a lower limit frequency, preferably equal to 1 Hz, and an upper limit frequency, preferably 1000 Hz, the optimum vibration frequency of the tilting board in correspondence of which the specific muscle has the maximum response to the stimulation and consequently setting vibration frequency of the mechanical means 5.

In a first embodiment of the device according to the invention, it is provided a method for the determination of the optimum frequency comprising the phases of:

application, in a conventional way, of the medical electrodes 6 of the detector 4 to the muscles to be stimulated;

repetition for N times, N being preferably eight times, of a data acquisition phase during which the central unit 1 actuates the vibration with a constant frequency of the mechanical means 5 for a $\Delta t$ time, $\Delta t$ being preferably between 5 and 10 seconds, with a progressively growing vibration frequency, from a repetition to the following one and included between the lower limit frequency and the upper limit frequency, processing, for each repetition, the average of the amplitude of signals coming from detector 4 and memorizing the same within the memory unit 2 along with the value of the corresponding vibration frequency; and determination of the maximum electrical response for which the central unit 1 determines among those memorized, the average having a maximum value, consequently individuating the optimum vibration frequency, for which the specific muscle has the maximum response.

Figure 4:
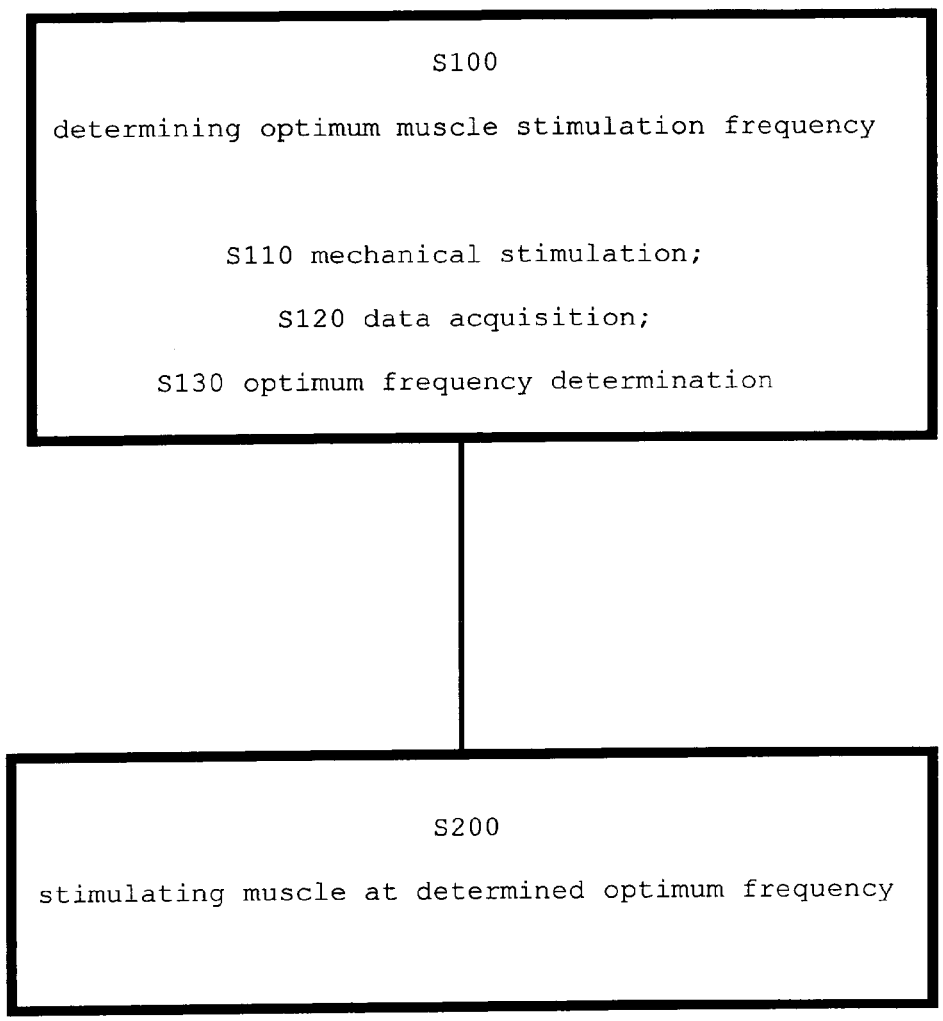
FIG. 4 shows the method steps of the invention.

With reference to FIG. 4, step S100 indicates the above-discussed determining of the optimum muscle stimulation frequency. As shown in FIG. 4, this determination comprises step S110 mechanical stimulation as discussed above, step S120 data acquisition, and step S130 optimum frequency determination.

Preferably, frequencies of consecutive repetitions during the data acquisition has a constant difference between each other; however, it can be provided also a variable and increasing difference in function of the absolute value of the frequency of the preceding repetition.

Once the optimum frequency has been determined, the muscular stimulation phase can be started (step 200 of FIG. 4), during which muscular stimulation phase the central unit 1 activates vibration of mechanical means 5 with said optimum frequency for a previously established time or a time selectable by the user by interface 3.

Figure 2:
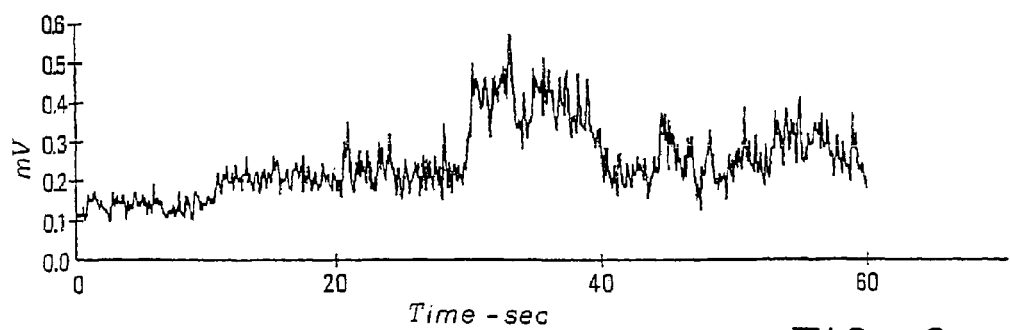
FIG. 2 shows the time run of the signal detected by the device of FIG. 1, applied to the lateral crureus muscle.
Figure 3:
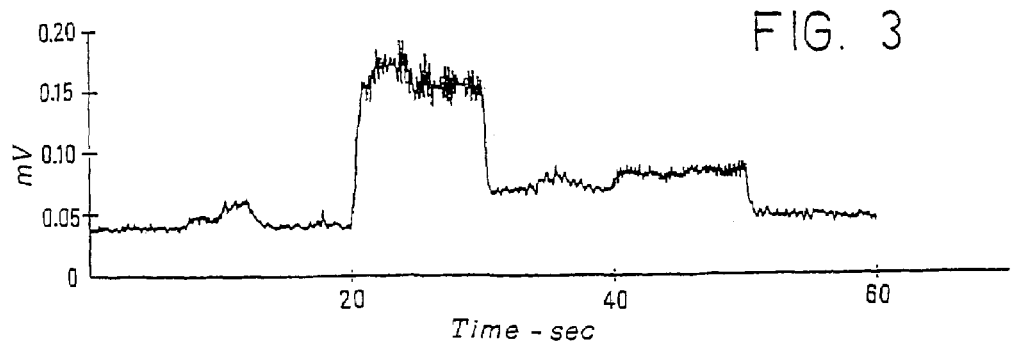
FIG. 3 shows the time run of the signal detected by the device of FIG. 1, applied to the front tibialis muscle.

For exemplificative purposes, FIGS. 2 and 3 show the time run of signals detected by detector 4, during the execution of the described method for the individuation of the optimum frequency, during which medical electrodes are respectively applied to the lateral crureus muscle and to the front tibialis muscle of a user. Particularly, the number of repetitions provided is 6 (N=6) and duration of the constant vibration frequency of the mechanical means 5 is 10 seconds ($\Delta t=10$). Vibration frequencies of the six repetitions are 22.5 Hz, 25 Hz, 27.5 Hz, 30 Hz, 32.5 Hz and 35 Hz, respectively.

It is evident from the above figures that optimum frequency (frequency at which average of amplitude has maximum value) for the lateral muscle is the fourth one, i.e. 30 Hz, while for the front tibialis muscle is the third one, i.e. 27.5 Hz.

Particularly, the lower limit frequency and the upper limit frequency could be variable in function of the specific fibers of the particular muscle to be stimulated, and settable by the interface 3.

A second preferred embodiment of the device according to the invention provides that the method for the individuation of the optimum frequency, comprising the following phases:

application, in a conventional way, of the medical electrodes 6 of the detector 5 to the muscles to be stimulated;

iteration for M times, M being preferably two times, of cycles of a number Ni of repetitions, wherein i is the i-th repetition, of data acquisition phases during which the central unit 1 actuates the constant frequency vibration of the mechanical means 5 for a time $\Delta t$, $\Delta t$ being preferably equal to 10 seconds, with a progressively growing frequency, from a repetition to the following one, and included between the lower limit frequency and the upper limit frequency, frequencies of consecutive repetitions having each other a constant difference $\Delta f_i$, where preferably, for the first iteration, first lower frequency coincides with the lower limit frequency and/or the second upper frequency coincides with the upper limit frequency, central unit 1 processing, for each iteration i the average of the amplitude of the signal coming from the detector 4 and memorizes the same within the memory unit 2 along with the value of the corresponding vibration frequency, the central unit 1 determining for each iteration i the average with the maximum value and individuating the corresponding best frequency for each iteration i, following the first one, the range between the first lower frequency and the second upper frequency comprising the best frequency individuated at the preceding iteration, for each iteration i, following the first one, the constant difference $\Delta fi$ between the consecutive repetition frequencies being lower than the difference $\Delta f_i -1$ of the preceding iteration ($\Delta f_i < \Delta f_{i-1}$); and determination of the optimum frequency at the end of the M-th iteration, wherein the best frequency individuated at the M-th iteration is memorized with the optimum frequency for which the maximum response has the best response.

In other words, the method described above determines optimum frequency individuating, by a progressively better resolution, the vibration frequency for which the specific muscle has the maximum response. Said method is faster with the cost of a slightly higher processing load.

Preferred embodiments of the device according to the invention provide visualization by the interface 3 that can comprise a display for signal detected by detector 4 and of the value of the optimum frequency individuated.

Other preferred embodiments can provide that the user can select manual setting of the vibration frequency by interface 3.

Further preferred embodiments can provide that values of optimum frequencies corresponding to the various muscles of a same user are memorized on removable memory, such as cards of magnetic and/or optical discs, by interface 3, to be then read by interface, avoiding further executions of the method for the determination of the optimum frequency. Eventually, optimum frequencies corresponding to a user can be memorized within memory unit 2 and recalled by association, and insertion by interface 3, of an identification code of the user.

Other embodiments can provide that muscular stimulation mechanical means provide an oscillating, rather than jumpy, board, or vibrating means.

Still, further preferred embodiment can provide more than one muscular electrical activity detector, each one applied to one muscle of the user, to stimulate different muscles at the same time. For example, different muscles of a leg can be stimulated inducing contractions at the frequency for which the whole of the responses from the muscles on which are applied the detectors is bigger. In this case, interface 3 can visualize on display all the signals detected by the detector.

Said embodiments can be used for diagnostic uses. For example, detectors can be applied on homologous muscles of the two upper limbs or of the two lower limbs. During the execution of the method for the determination of the optimum frequency, in case that one of the two limbs has been subjected to surgical intervention, and thus a mechanical insult has been made on the biological tissue (for example muscles and/or chorda and/or capsule and/or ligaments), response detected for the limb subjected to a surgical intervention is different with respect to the laudable one. Amount of the response difference of the two limbs indicates the amount of the difference of response of propioceptors ad, thus, amount of damage received from the person at the limb subjected to surgical intervention.

The present invention has been described for illustrative but not limitative purposes, according to its preferred embodiments, but it is to be understood that modifications and/or changes can be introduced by those skilled in the art without departing from the relevant scope as defined in the enclosed claims.

The invention claimed is:

1. A method for optimally mechanically stimulating a user's muscle, comprising the steps of:
   A) a first determining step of determining a frequency of muscular stimulation that corresponds to an optimum frequency for a maximum stimulation of the user's muscle, the first determining step comprising:
      i) using a mechanical means to subject the user's muscle to a mechanical stimulation at each of plural frequencies over a range from a lower limit frequency through an upper limit frequency,
      ii) during the mechanical stimulation, conducting a data acquisition phase by using a muscular electrical activity detector, applied on the user's muscle, to measure the muscular stimulation of the user's muscle at each of the plural frequencies, the measured muscular stimulation being based on a signal amplitude output from the detector, and
      iii) from the measured muscular stimulation at each of the plural frequencies, determining the optimum frequency for maximum stimulation of the user's muscle based on a maximum measured muscular stimulation as reflected by a function of the measured signal amplitude output from the detector; wherein the optimum frequency is being determined from the frequency corresponding to a maximum measured signal amplitude output from the detector; and
   B) a second stimulating step of stimulating the user's muscle at the determined optimum frequency to subject the user's muscle to an optimum stimulation.

2. The method of claim 1, wherein, the lower limit frequency is equal to 1 Hz and the upper limit frequency is equal to 1000 Hz.

3. The method of claim 1, wherein, the data acquisition phase comprises
   a) using the mechanical means, stimulating the user's muscle at a stimulation frequency for a first time period, and
   b) recording the detector signal amplitude output at the stimulation frequency during the first time period, wherein,
   steps a) and b) are performed with the stimulation frequency being at the lower limit frequency,
   steps a) and b) are performed with the stimulation frequency being at the upper limit frequency,
   steps a and b) are performed with the stimulation frequency being at each of plural frequencies between the lower limit frequency and the upper limit frequency, and
   wherein determination of the optimum frequency for maximum stimulation of the user's muscle in the step iii) is based on a maximum value of the recorded detector signal amplitude output averaged over the first time period at each of the plural frequencies, the optimum frequency being the stimulation frequency corresponding to the maximum averaged value of the recorded detector signal amplitude output.

4. The method of claim 3, wherein,
   the step ii) uses plural muscular electrical activity detectors, applied on the user's muscle, to measure the muscular stimulation of the user's muscle at each of the stimulation frequencies during performance of the step a), and
   the step b) records the detector signal amplitude outputs of each of the plural detectors at the stimulation frequency during the first time period.

5. The method of claim 4, wherein,
the steps a) and b) are performed eight total times.

6. The method of claim 5, wherein,
the first time period of the step a) is equal to 5 seconds.

7. The method of claim 6, wherein,
in repeatedly performing the step a), the stimulation frequency increases with each frequency, and a frequency difference between any one stimulation frequency and a next stimulation frequency is increased by an increasing fixed amount.

8. The method of claim 5, wherein,
the first time period of the step a) is equal to 10 seconds.

9. The method of claim 5, wherein,
in repeatedly performing the step a), the stimulation frequency increases with each frequency, and a frequency difference between any one stimulation frequency and a next stimulation frequency is increased by a fixed amount.

10. The method of claim 3, wherein,
in repeatedly performing the step a), the stimulation frequency increases with each frequency, and a frequency difference between any one stimulation frequency and a next stimulation frequency is constant.

11. The method of claim 3, wherein,
in repeatedly performing the step a), a first frequency difference between a first stimulation frequency and a second stimulation frequency is greater than a second frequency difference between the second stimulation frequency and a third stimulation frequency.

12. The method of claim 3, wherein,
in repeatedly performing the step a), the stimulation frequency increases with each frequency, and a frequency difference between any one stimulation frequency and a next stimulation frequency is varied.

13. The method of claim 1, wherein,
during the mechanical stimulation, conducting the data acquisition phase by using a muscular electrical activity detector measures the muscular stimulation of the user's muscle at each of the plural frequencies, the measured muscular stimulation being based on an electromyographycal response of the muscle.

14. The method of claim 1, wherein, the data acquisition phase comprises
   a) using the mechanical means, stimulating the user's muscle at a stimulation frequency for a first time period, and b) recording the detector signal amplitude output at the stimulation frequency during the first time period, wherein, steps a) and b) are performed with the stimulation frequency being at the lower limit frequency, steps a) and b) are performed with the stimulation frequency being at the upper limit frequency, wherein determination of the optimum frequency for maximum stimulation of the user's muscle in the step iii) is based on a maximum value of the recorded detector signal amplitude output averaged over the first time period at each of the plural frequencies, the optimum frequency being the stimulation frequency corresponding to the maximum averaged value of the recorded detector signal amplitude output.

15. The method of claim 1, wherein, the first determining step determines a frequency of muscular stimulation that corresponds to an optimum frequency for a maximum stimulation of the user's plural muscles, the first determining step comprising:

i) using the mechanical means to subject the user's plural muscles to the mechanical stimulation at each of the plural frequencies, ii) during the mechanical stimulation, conducting the data acquisition phase by using muscular electrical activity detectors, applied on each of the user's plural muscles, and iii) from the measured muscular stimulation, determining the optimum frequency for maximum stimulation of the user's plural muscles based on the maximum measured muscular stimulation as reflected by the function of the measured signal amplitude output from the detectors; and the second stimulating step stimulates muscles at the determined optimum frequency to subject the user's plural muscles to an optimum stimulation.

16. The method of claim 1, wherein, the data acquisition phase is repeated for M cycles, each cycle of the M cycles comprising:

a) using the mechanical means, stimulating the user's muscle at a stimulation frequency for a first time period, and b) recording the detector signal amplitude output at the stimulation frequency during the first time period, wherein, steps a) and b) are performed with the stimulation frequency being at the lower limit frequency, steps a) and b) are performed with the stimulation frequency being at the upper limit frequency, steps a) and b) are performed with the stimulation frequency being at each of N plural frequencies between the lower limit frequency and the upper limit frequency, the N plural frequencies having a constant frequency difference, wherein, determination of the optimum frequency for maximum stimulation of the user's muscle in the step iii) during each cycle is based on a maximum value of the recorded detector signal amplitude output averaged over the N plural frequencies; and wherein for each cycle after the first cycle, the lower limit frequency is increased and the upper limit frequency is decreased so that a frequency range stimulating the user's muscle is decreased with each new cycle and so that the stimulation frequency between each of the N plural frequencies decreases with each new cycle, the optimum frequency being the stimulation frequency corresponding to the maximum value of the recorded detector signal amplitude output over the M cycles.

17. An automatic device for optimizing mechanical muscular stimulation, comprising:

a mechanical muscle stimulator for making a determination of a frequency of muscular stimulation that corresponds to an optimum frequency for a maximum stimulation of a user's muscle, the mechanical muscle stimulator subjecting the user's muscle to a mechanical stimulation at each of plural frequencies over a range from a lower limit frequency through an upper limit frequency;

a central electronic unit for conducting data acquisition during the muscle stimulation using a muscular electrical activity detector applied on the user's muscle, to measure the muscular stimulation of the user's muscle at each of the plural frequencies, the measured muscular stimulation being based on a signal amplitude output from the detector;

wherein the central electronic unit, from the measured muscular stimulation, determines the optimum frequency for maximum stimulation of the user's muscle based on a maximum measured muscular stimulation as reflected by a function of the measured signal amplitude output from the detector; and wherein, from the determined optimum frequency, the mechanical muscle stimulator is set to stimulate the user's muscle at the determined optimum frequency to subject the user's muscle to an optimum stimulation.

18. The device of claim 17, wherein the mechanical muscle stimulator is actuated by the central electronic unit, the central electronic unit being connected to a memory unit and connected to the detector, and the central electronic unit managing and controlling the automatic device and processing data coming from the detector, and wherein the mechanical muscle stimulator stimulates the user's muscle at frequencies ranging from 22.5 Hz to 35 Hz.

19. The device of claim 18, wherein, there are plural detectors, each detector configured to be applied on a corresponding muscle of the user, and the detectors are muscular electrical activity detectors.

20. The device of claim 19, wherein, the detectors comprise medical electrodes, amplified in situ.

21. The device of claim 17, further comprising: an input/output interface, wherein the interface comprises a display, wherein the central electronic unit displays signals detected from the detector and a value of the optimum frequency on the display, and wherein the interface includes a manual setting selection of the periodical contractions of the muscle.

* * * * *